(12) United States Patent
Mark et al.

(10) Patent No.: US 10,181,022 B2
(45) Date of Patent: Jan. 15, 2019

(54) SYSTEM FOR AUTOMATED LOGIN INITIALIZATION ON DETECTION OF IDENTIFICATION DEVICE

(71) Applicant: Mobile Heartbeat, LLC, Waltham, MA (US)

(72) Inventors: Jacob Mark, Needham, MA (US); Sajikumar Aravind, Burlington, MA (US)

(73) Assignee: Mobile Heartbeat, LLC, Waltham, MA (US)

( * ) Notice: Subject to any disclaimer, the term of this patent is extended or adjusted under 35 U.S.C. 154(b) by 0 days.

(21) Appl. No.: 15/894,313

(22) Filed: Feb. 12, 2018

(65) Prior Publication Data

US 2018/0268125 A1 Sep. 20, 2018

Related U.S. Application Data

(63) Continuation of application No. 13/616,483, filed on Sep. 14, 2012, now Pat. No. 9,904,777.
(Continued)

(51) Int. Cl.
*G06F 21/34* (2013.01)
*H04L 9/32* (2006.01)
(Continued)

(52) U.S. Cl.
CPC .............. *G06F 21/34* (2013.01); *G06F 21/35* (2013.01); *G16H 10/60* (2018.01); *H04L 9/32* (2013.01);
(Continued)

(58) Field of Classification Search
CPC ... H04L 63/0853; H04L 63/0492; H04L 9/32; G06F 19/322; G06F 21/34; G06F 21/35;
(Continued)

(56) References Cited

U.S. PATENT DOCUMENTS 5,815,665 A 9/1998 Teper et al.
7,454,783 B2 11/2008 Dupouy et al.
(Continued)

FOREIGN PATENT DOCUMENTS

WO 2009130796 10/2009

OTHER PUBLICATIONS

International Search Report for PCT/US2012/055366 dated Nov. 13, 2012, all pages.

*Primary Examiner* — Theodore C Parsons
(74) *Attorney, Agent, or Firm* — Kilpatrick Townsend & Stockton LLP

(57) ABSTRACT

A system for automating a data device login procedure having a network, a system backend communicable with the network having a backend processor configured to control a simplified login procedure and a database of login information accessible by the backend processor, a data reader communicable with the system backend configured to receive a credential data from an identification device, and a fungible portable data device communicable with the backend configured to receive a login information from the system backend for completing a login procedure. The data reader is configured to initiate the login procedure upon receipt of the credential data from the identification device and communicate the credential data to the backend. The backend is configured to determine the login information associated with the credential data comprising personalization information for the fungible portable data device and the system backend completes the login procedure to the fungible portable data device.

20 Claims, 8 Drawing Sheets

Related U.S. Application Data

(60) Provisional application No. 61/534,731, filed on Sep. 14, 2011.

(51) Int. Cl.
*G16H 10/60* (2018.01)
*H04L 29/06* (2006.01)
*H04W 12/08* (2009.01)
*G06F 21/35* (2013.01)

(52) U.S. Cl.
CPC ......... *H04L 63/0853* (2013.01); *H04W 12/08* (2013.01); *G06F 2221/2149* (2013.01); *H04L 63/0492* (2013.01)

(58) Field of Classification Search
CPC ........... G06F 2221/2149; G16H 10/60; H04W 12/08
See application file for complete search history.

(56) References Cited

U.S. PATENT DOCUMENTS

| | | | |
|---|---|---|---|
| 7,657,657 B2 | 2/2010 | Rao et al. | |
| 7,694,130 B1 | 4/2010 | Martinez | |
| 7,756,748 B2 | 7/2010 | Shaked et al. | |
| 7,962,544 B2 | 6/2011 | Torok et al. | |
| 8,045,961 B2 | 10/2011 | Ben Ayed et al. | |
| 8,112,066 B2 | 2/2012 | Ben Ayed | |
| 8,190,129 B2 | 5/2012 | Ben Ayed | |
| 8,213,902 B2 | 7/2012 | Rowley | |
| 8,219,584 B2 | 7/2012 | Starr | |
| 8,239,252 B2 | 8/2012 | Wellman | |
| 8,266,681 B2 | 9/2012 | Deshpande et al. | |
| 2002/0017557 A1* | 2/2002 | Hendrick | G06F 21/34 235/380 |
| 2003/0148773 A1 | 8/2003 | Spriestersbach et al. | |
| 2003/0195967 A1 | 10/2003 | Selgas et al. | |
| 2004/0111320 A1* | 6/2004 | Schlieffers | A47F 9/047 705/16 |
| 2004/0128393 A1 | 7/2004 | Blakley, III et al. | |
| 2006/0031683 A1 | 2/2006 | Marion et al. | |
| 2006/0035707 A1* | 2/2006 | Nguyen | G07F 17/32 463/29 |
| 2006/0208063 A1* | 9/2006 | Patel | G06F 21/35 235/380 |
| 2008/0100414 A1 | 5/2008 | Diab et al. | |
| 2009/0132813 A1 | 5/2009 | Schibuk | |
| 2009/0210940 A1 | 8/2009 | Dean | |
| 2011/0221568 A1* | 9/2011 | Giobbi | G06F 21/32 340/5.82 |
| 2011/0314530 A1* | 12/2011 | Donaldson | G06F 21/83 726/7 |
| 2012/0042366 A1 | 2/2012 | Jin et al. | |
| 2013/0115880 A1 | 5/2013 | Dal Bello et al. | |
| 2014/0041009 A1 | 2/2014 | Kousaka | |
| 2014/0313539 A1* | 10/2014 | Kawano | G06F 21/44 358/1.14 |

\* cited by examiner

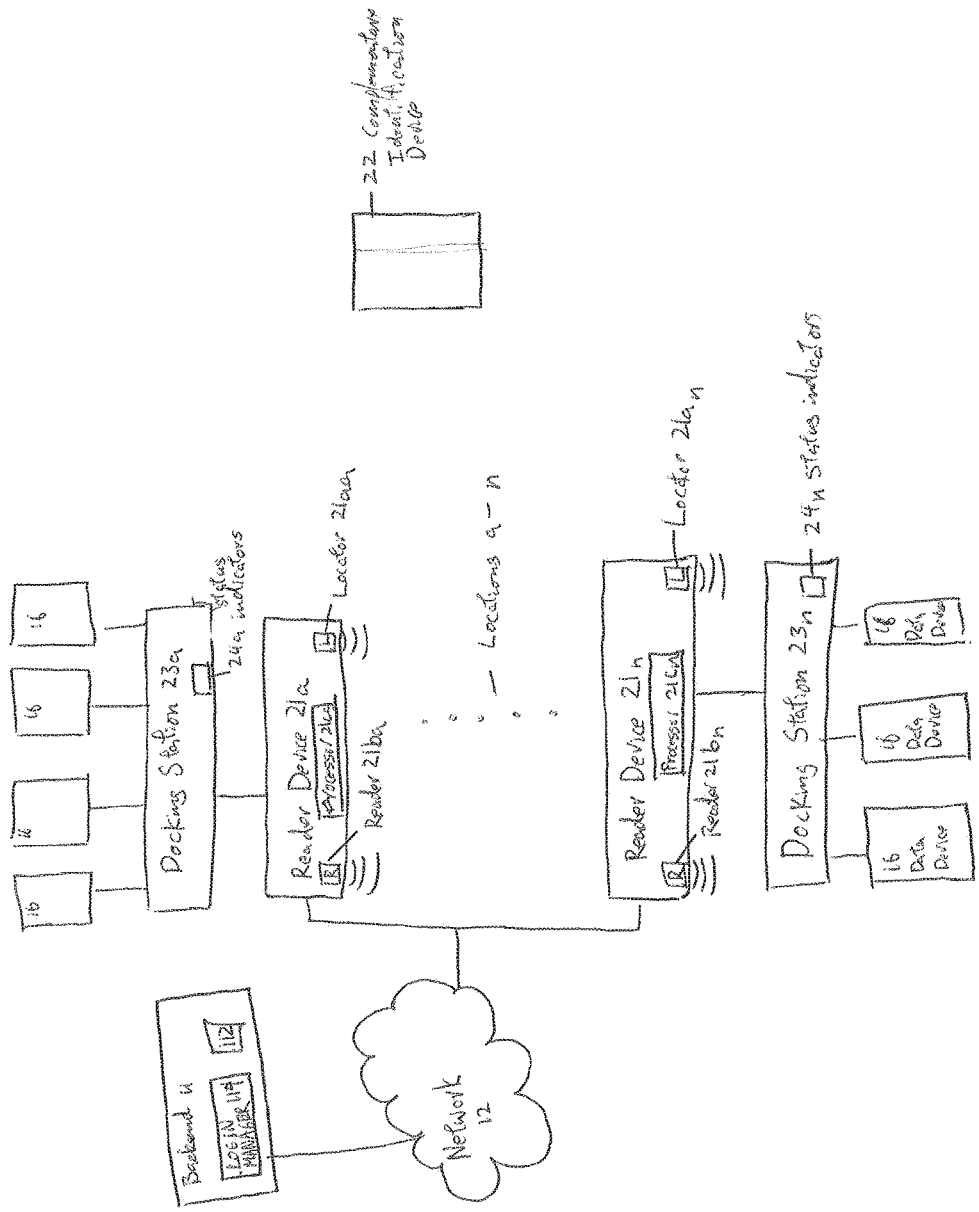

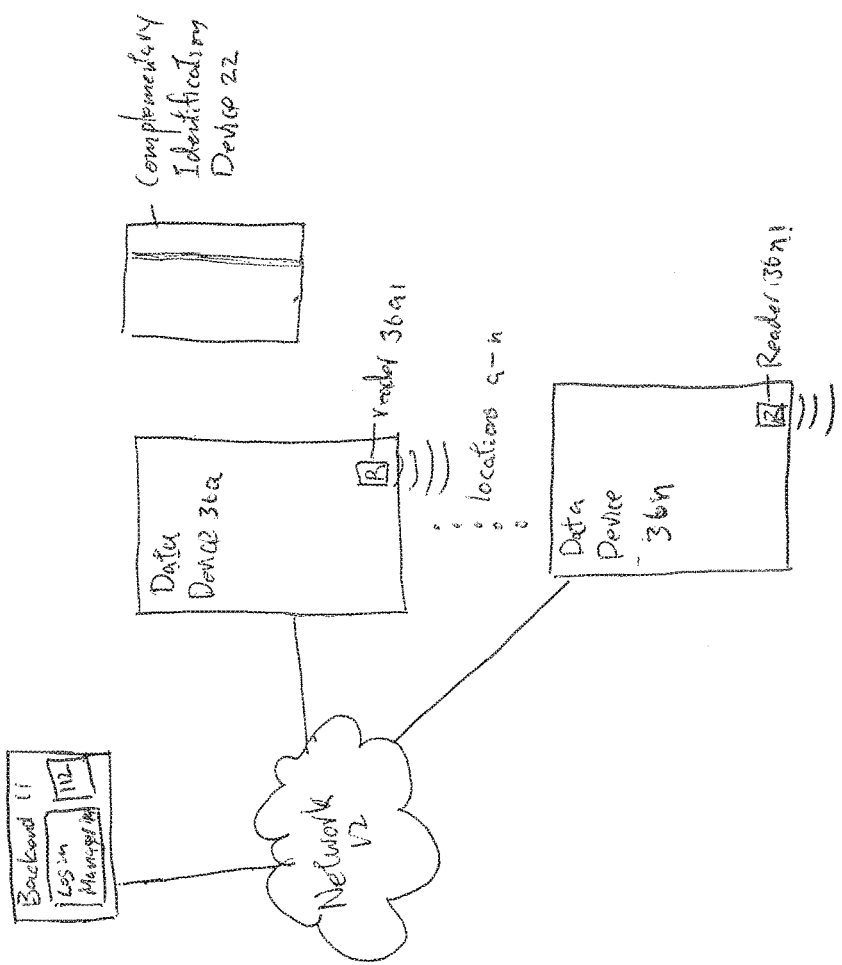

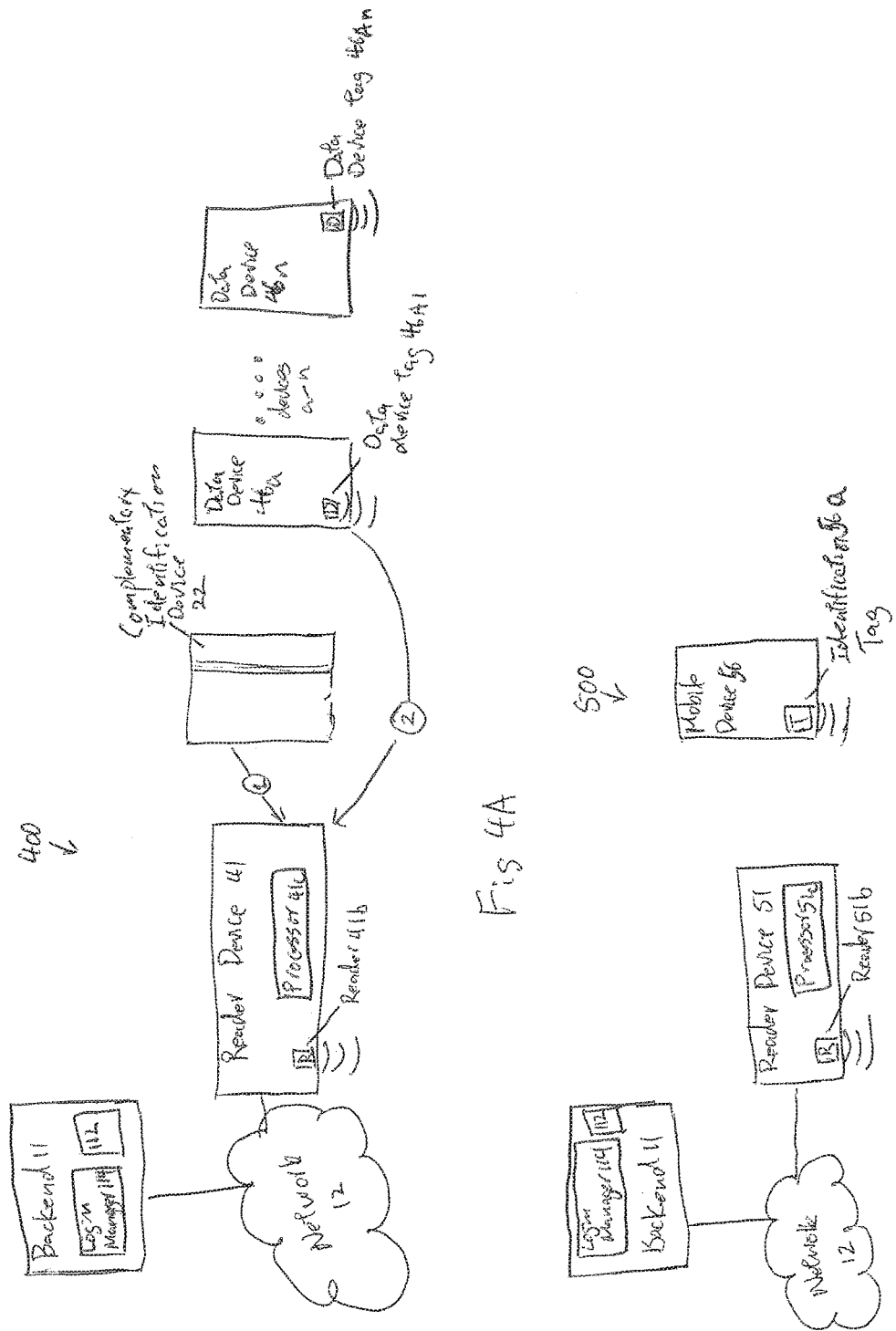

SYSTEM FOR AUTOMATED LOGIN INITIALIZATION ON DETECTION OF IDENTIFICATION DEVICE

CROSS-REFERENCE TO RELATED APPLICATIONS

The present application is a continuation of U.S. patent application Ser. No. 13/616,483, filed on Sep. 14, 2012, entitled "SYSTEM FOR AUTOMATED LOGIN INITIALIZATION ON DETECTION OF IDENTIFICATION DEVICE," which claims the benefit of priority of U.S. Provisional Application No. 61/534,731, filed on Sep. 14, 2011, entitled "AUTOMATED LOGIN INITIALIZATION ON DETECTION OF IDENTIFYING INFORMATION," the full disclosures of which are incorporated herein in their entirety.

BACKGROUND

The present embodiments relate to a login system for data devices, more particularly, to an automated login initialization system for fungible data devices upon the detection of identifying information.

BRIEF DESCRIPTION OF THE DRAWINGS

The foregoing aspects and other features of the present disclosed embodiment are explained in the following description, taken in connection with the accompanying drawings, wherein:

FIG. 2a is a schematic representation of a first aspect of an automated login initialization system.

FIG. 3a is a schematic representation of a second aspect of an automated login initialization system.

FIG. 4a is a schematic representation of a third aspect of an automated login initialization system.

FIG. 5a is a schematic representation of a fourth aspect of an automated login initialization system.

DETAILED DESCRIPTION

The disclosed embodiments generally provides for a system for automatic login initializations on detection of identifying information. Generally, when there are collaborative systems with many users and many data devices which require user access, it is desirable to have a means to simplify or automate login procedure as well as a means for enabling a system for managing the security of devices. One such system where it is desirable to have such a means to simplify and automate login procedure may be the Workflow and Resource Management System with Integrated Bi-Directional communications as described in U.S. patent application Ser. No. 13/027,158, filed on Feb. 14, 2011, the disclosure of which is incorporated by reference herein in its entirety. Such a means to simplify and automate login procedure may be utilized to identify, track and manage individual users within the systems as well as manage what individual users may see and access when the individual user logs into a data device. For simplicity and ease of understanding, the nomenclature for such a system will be subsequently referred to within the specification as a "Quick Launch" system. The Quick Launch system may be used as a simplified platform by which each one of multiple users may individually log into one of many devices within the system. As such, the Quick Launch system may be implemented in any suitable system where it is desirable to manage multiple users each individually using one of many devices within the system within any context. In one aspect, the context may be a hospital or healthcare context, but in other aspects, may include retail or any suitable context. The Quick Launch system may be integrated into the system such that it leverages existing technology and devices to automate and facilitate logins, obviating the need for expensive or undesirable specialized devices. Additionally, the Quick Launch system may be flexible enough to integrate with specialized pre-existing components to extend functionality. For example, one such example of integrating with pre-existing components may include integration with a clock-in system so that log-ins may also function as clocking into a shift. Further, the Quick Launch system may be integrated with the system so as to allow for fungible data devices. In typical systems, a device may often be user-specific and cannot be interchangeable with another device. However, the Quick Launch system allows for each device to be interchangeable with another so that each device can be used by any user in place of another, while still maintaining personalization keyed to each unique user. In alternate aspects, the Quick Launch System may also be used to lock or unlock functionalities within a device that is not fungible so that the device may continue to be used outside of the system.

Figure 1:
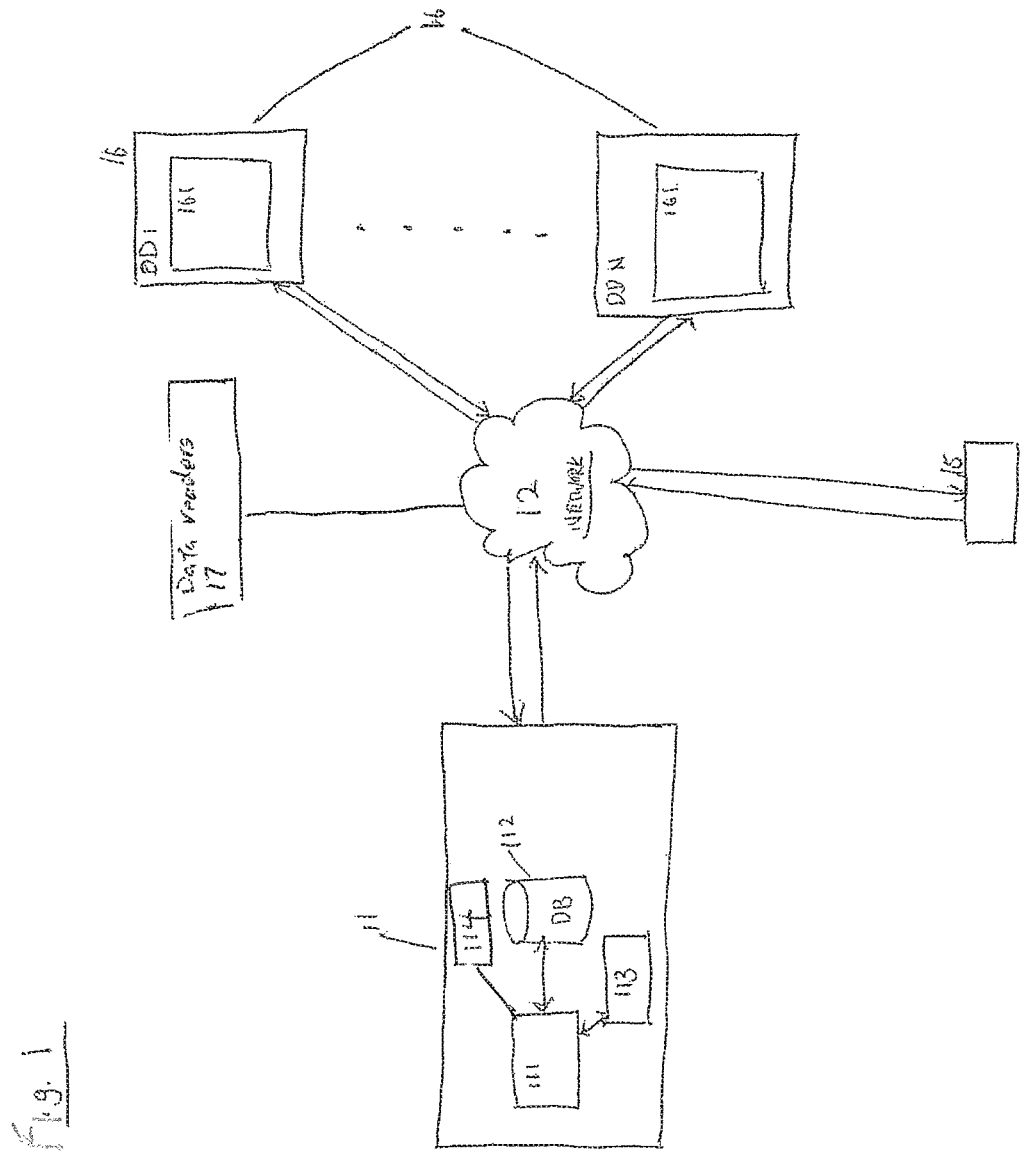
FIG. 1 is a schematic representation illustrating an overview of system utilizing an automated login initialization system.

FIG. 1 illustrates an exemplary schematic diagram illustrating a system utilizing a Quick Launch system. Although the present invention will be described with reference to the embodiment shown in the drawings, it should be understood that the present exemplary embodiments can be used individually or in any suitable combination thereof. Although the aspects of the disclosed embodiment will be described with reference to the drawings, it should be understood that the aspects of the disclosed embodiment can be embodied in many alternate forms. In addition, any suitable size, shape or type of elements or materials could be used.

Referring to FIG. 1, a backend 11 is depicted, the backend may be the form of a general purpose computer system or server system. In alternate embodiments, the backend may also be multiple computers or servers or any other suitable device. Furthermore, backend 11 may be able to communicate over a network 12 with data devices that also communicate over network 12. In one embodiment, the network 12 may be a wireless network. The wireless network preferably is an 802.11 network, but may also be Bluetooth, GSM, RF, GSM or any other suitable form of network. In another embodiment, the network 12 may also be a wired network. Through the network 12, the backend 11 may be able to enable a variety of data communication technology, for example, but not limited to voice-over-IP, video-over-IP, text messaging, public switched telephone networks, or any other form of bi-directional communication. This may take the form of, for example, a voice over IP telephony server 113. The backend may also run an enterprise application 111 within a server environment. The enterprise application 111 may be implemented using a computer code comprising instructions that may be executed by a processor within the backend 11. The code may be embodied in a computer-readable medium such as a magnetic or optical disk, programmable memory chip, or any other non-transitory computer-readable medium. The enterprise application may communicate with a database 112 and access and update the information within the database. The database 112 may be a login database comprising a database containing information pertaining to user logins, personalized settings and data, and any other suitable credential information. The enterprise application 111 acts as the controller for the workplace and resource system. The server environment upon which the enterprise application 111 runs may take the form of, for example, Java servlets, or any other suitable environment upon which an enterprise application may execute. Login management application 114 may also be on the backend 11 to manage users and device logins. In accordance to an embodiment, the system backend 11 may be configured for any sort of suitable reasonable use and may not be dedicated specifically for login procedures.

Referring still to FIG. 1, a number of data devices 16 may communicate over the network 12. As described previously, the network 12 may be a wireless network in some embodiments. The wireless network preferably is an 802.11 network, but may also be Bluetooth, GSM, RF, GSM or any other suitable form of network. In other embodiments, the network 12 may also be a wired network. In one aspect of the disclosed embodiments, the data devices 16 may be generally fungible devices as previously noted, that is, one data device 16 may be interchangeable with any other data device 16. Thus, data device 16 may store no personalized settings or data desirable for operation, instead relying on data received from the system backend 11 by means of a device data application 161. However, in other aspects of the disclosed embodiment, the data device 16 may be unique to the user, but configured so that functionalities available within the system are locked or blocked when no longer logged in. The data application 161 may communicate with backend 11 through the data module 116, for example via Web Services such as SOAP protocols, or any other suitable communications protocols and is capable of accessing and updating data stored within the database 112, possibly through the login manager 114. The device data application 161 may take the form of a native application designed to run as computer code executed by data device 16. The computer code may be embodied in a computer-readable medium stored on data device 16 such as magnetic or optical disk, programmable computer chip or any other non-transitory computer-readable medium. In other embodiments, the device data application 161 may also take the form of a non-native application, for example, a Java-based application running on a virtual machine or a web-based application such as an HTML5 application. In some embodiments, the data devices may take the form of smartphones. In other embodiments, the data devices 16 may also be in the form of Personal Digital Assistants (PDAs), computer terminals, or any other suitable device capable of running the device data application 161 described above. Other devices may also be able to communicate with backend 11 through the network 12 as described above. Such devices may include sensors 15 or any other suitable devices.

Referring now to FIG. 2A, an exemplary schematic diagram of a first aspect of the Quick Launch system is shown. As can be seen, a number of data devices 16, as described previously, are shown resting in one or more docking stations 23a-n in a generally inactive state. As noted previously, each of the data devices 16 may be configured to communicate with the backend 11 via the network 12. For simplicity and ease of understanding, the remainder of the application will be discussed with respect to docking station 23a and an associated reader device 21a, although what is disclosed is equally applicable to any docking station 23a-n and its respective associated reader device 21a-n. In one aspect of the disclosed embodiment, the docking station 23a may be configured to hold one data device 16. However, in other aspects of the disclosed embodiment, the docking station 23a may be configured to hold any suitable number of data devices 16. In one aspect of the disclosed embodiment, the docking station 23a may be configured to recharge each of the data devices 16 held by the docking station 23a. Further, the docking stations 23a-n may further have status indicators 24a-n configured to convey information related to the status of each data device 16. In one aspect, such information may include the charge status of each data device 16. In alternate aspects, such information may include any suitable information related to each data device 16, includes readiness, or any other suitable data. The docking station 23a may be further associated with a reader device 21a. In one aspect, there may be a means of communication connection between a reader device 21a and a docking station 23a, such, but not limited to, a wireless connection. In alternate aspects, any suitable means of communication or coupling may be available between the reader device 21a and docking station 23a. Reader device 21a may, for instance, correspond substantially with the data readers 17 as described previously. In one aspect of the disclosed embodiment, the reader device 21a may further contain a data reader 21ba. The data reader 21ba may be configured to read or otherwise receive information from a complementary device configured to transmit or contain readable data. For example, in one aspect of the disclosed embodiment, the data reader 21ba may be an RFID reader. However, in other aspects of the disclosed embodiment, the data reader 21ba may also be a Near Field Communication (NFC) data reader, a Bluetooth module, an radio frequency (RF) reader, infrared (IR) receiver, or any suitable reader capable of receiving transmitted data information. In yet alternate aspects of the disclosed embodiment, the reader 21ba may also be a camera or optical scanner configured to read visual indicia including barcodes, Quick Response (QR) codes, matrix bar codes, Microsoft Tags, or any other suitable visual or printed indicia. In yet more alternate aspects, the reader 21ba may be any suitable device capable of receiving or scanning any sort of data, including, for instance, magnetic stripe readers. In one aspect, the reader device 21a may be any suitable device capable of reading data and may not be dedicated device specifically for use in login procedures.

Referring still to FIG. 2A, reader 21ba may be configured to read data from a complementary identification device 22. In one aspect, reader 21ba may be part of a dumb reader merely capable of reading data. However, in alternate aspects, the reader 21ba may be connected to a reader processor 21ca which may take the form of a PDA, PC or any other suitable processing device that controls reader 21ba devices and communicates with the backend 11 via network 12. Generally speaking, the complementary identification device 22 may be an identification badge or other similar for of user identification. However, in other aspects of the disclosed embodiment, the complementary identification device 22 may be any suitable device that is specific to a particular user. For example, a user's personal mobile phone or device may also be used as a complementary identification device 22. The complementary identification device 22 may be configured to contain any format of data readable by the corresponding 21ba. For example, in one aspect of the disclosed embodiment, the complementary identification device 22 may have an RFID tag, an NFC chip, a Bluetooth data module, an RF data transmitter, an IR data transmitter, or any suitable means for transmitting an amount of data readable by the reader 21b. In alternate aspects, the complementary identification device 22 may also have visual or printed indicia such as, for example, barcodes, QR codes, matrix barcodes, Microsoft Tags, or any other suitable visual/printed indicia containing a small amount of data readable by the reader 21ba. In yet other aspects, the complementary identification device 22 may include any suitable data readable by the reader 21ba, including, for instance, data encoded on a magnetic stripe. The data stored within the complementary identification device may include any suitable data which may be used to facilitate a log-in procedure. For instance, in one aspect, the data may include simple login data identifying the user. In other aspects, the data stored within the complementary identification device may be of any suitable format or type, for example, encrypted keys, credential files, or any other suitable data which may be used to log a user into a data device 16.

The reader device 21a may also have a locator 21aa. The locator may be used to find the location of the docking device. Further, the locator 21aa may also be utilized to locate data devices 16 within the vicinity of the reader device, for example, any data devices within an associated docking station 23a. The locator 21aa may use any suitable means of locating both its position and any devices within its vicinity. In one aspect, the locator 21aa may use Bluetooth to locate data devices within its vicinity, but in other aspects, may also use RFID, NFC, or any other suitable system. In alternate aspects of the disclosed embodiments, the locator 21aa may also be part of a docking station 23a or any other suitable location for a locator device.

The reader device 21a may further be connected to a network 12. As noted previously, the network may be a wired network or may be wireless. The wireless network may be an 802.11 network, but may also be Bluetooth, GSM, RF, GSM or any other suitable form of network. The reader device 21a may further be configured to communicate with a login database 112 located on backend 11. This process may be managed by login management application 114. In one aspect of the disclosed embodiment, the login database 112 may, for instance, be accessed by the reader device 21 to retrieve credential or identification information, or information about user settings or other data desirable to complete a login procedure. In alternate aspects, the login database 112 may also be used to verify login data received from the complementary identification device 22 to facilitate a login. In yet other aspects of the disclosed embodiments, the login database 112 may be accessed for any other suitable data desirable to facilitate a user to log into a data device 16.

Figure 2B:
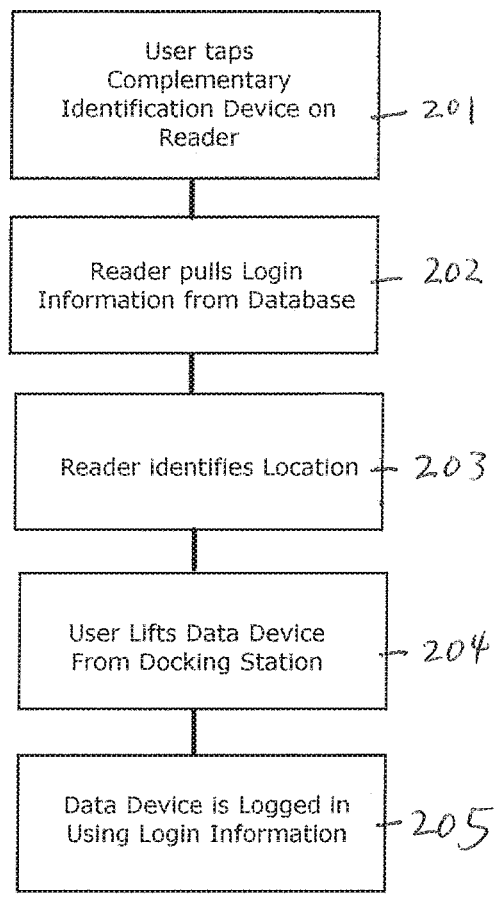
FIG. 2b is an exemplary flowchart illustrating the operation of an automated login initialization system in accordance with the first aspect.

Referring now to FIG. 2B, a flowchart illustrating the exemplary usage of the first aspect of the disclosed embodiment is shown. Referring now to Block 201, the user may initialize a log-in procedure by first using the complementary identification device 22 to transmit or pass information to the reader 21ba of the reader device 22a. In one aspect, this may be done by tapping or waving the complementary identification device 22 on or within the vicinity of the reader 21b. This may be achieved, for example, with data stored within RFID tags, NFC chips, Bluetooth modules, RF transmitters or IR transmitters, or optical or printed indicia, or any other suitable means of transferring or passing data, for example, through magnetic stripes. The data transmitted or passed to reader 21ba of the reader device 21a may include, for instance, log-in identification data, or any other suitable data desirable to facilitate a log-in procedure as discussed above. At block 202, the reader device 21a may be configured to access the login database 112 located on backend 11 via network 12. This process may be controlled by login management application 114. Specifically, the reader device 21a may download login information associated with the data received from the complementary identification device 22. In one aspect of the disclosed embodiment, the login information downloaded from the login database 112 may include any suitable information desirable to complete a login procedure of a data device 12. For instance, the login information may include credential information, or may include setting information or other data device specific data desirable to complete a login. At block 203, the reader device 21a may identify locations with the locator 21aa. For example, this may allow the reader device 21a to identify where the location of the reader device 21a within a building or complex. Further, the locator 21aa may be used to determine which data devices 16 located on a docking station 23a within a predetermined vicinity of the reader device 21a. For example, this may be done by detecting nearby devices by means of Bluetooth signals, RFID signals, or any other suitable means. Further, upon detection of data devices 16 within the vicinity of the reader device 21a (and thus also within the vicinity of the user by extension), the system may put the data devices 16 in a state that is ready for logging onto the system. A user may be able to determine which data devices 16 are in a state that is ready for logging onto the system by means of information conveyed from the status indicator 24a, or by a change in appearance within each of the data devices 16 (for instance, a changed user display image, or any other suitable change in appearance). In one aspect of the disclosed embodiment, the system may further determine whether each of the data devices 16 have full or near full battery charges. The system may only place the data devices 16 within the vicinity of the reader device 21 that have fully charged or nearly full charged batteries in a state that is ready for logging onto the system instead of all devices within the vicinity of the reader device 21a. This may be done by any suitable means, including, but not limited to, polling of status of each data device 16 by the reader device 21a. At block 204, the user lifts the data device 16 from the docking station 23a. At block 205, the action of lifting the data device 16 from the docking station 23a completes the log-in procedure. The system backend 11 may push the user log-in data to the data device 16 lifted from the docking station 23a. For example, the user log-in data may include data desirable to complete the log-in procedure. Further the user log-in data may also include data which personalizes the data device 16. For example, the data device 16 may be logged in with personalized settings, or messages, or any other suitable data desirable for a personalized login. The completion of the log-in procedure thus allows the user to access the data device 16 so that all of the user's personalized settings and data are now accessible on the data device 16. Upon the completion of the log-in procedure on the data device 16 lifted by the user, all other data devices 16 may be placed back in an inactive state. At the completion of use of the logged-in data device 16, the user may place the logged-in data device 16 back into a docking station 23*a* to log the user back out of that data device 16.

Referring now to FIG. 3A, an exemplary schematic diagram of a second aspect of the Quick Launch system is shown. The second aspect may include one or more data devices 36*a-n* similar to those described previously as data devices 16*a-n*. For simplicity and ease of understanding, the remainder of this section will refer to data device 36*a*, although as can be realized, what is disclosed is equally applicable to all data devices 36*a-n*. Further, the data device 36*a* may also have a reader 36*a*1. Reader 36*a*1 may be data reader substantially similar to reader 21*ba*. For example, in one aspect of the disclosed embodiment, the reader 36*a*1 may be an RFID reader. However, in other aspects of the disclosed embodiment, the data reader 36*a*1 may also be a Near Field Communication (NFC) data reader, a Bluetooth module, an radio frequency (RF) reader, infrared (IR) receiver, or any suitable reader capable of receiving transmitted data information. In yet alternate aspects of the disclosed embodiment, the reader 36*a*1 may also be a camera or optical scanner configured to read visual indicia including barcodes, Quick Response (QR) codes, matrix bar codes, Microsoft Tags, or any other suitable visual or printed indicia. In one aspect, the reader device 36*a*1 may be any suitable device which is a part of data device 36*a* capable of reading data and may not be dedicated reader specifically for use in login procedures. The reader 36*a* may be configured to read data from a complementary identification device 22 substantially similar to that described previously. Further, each data device 36*a* may also be communicably connected to the network 12. As noted previously, the network may be a wired network or may be wireless. The wireless network may be an 802.11 network, but may also be Bluetooth, GSM, RF, GSM or any other suitable form of network. The data device 36*a* may further be configured to communicate with the login database 112 located on backend 11 via the network 12 as described previously.

Figure 3B:
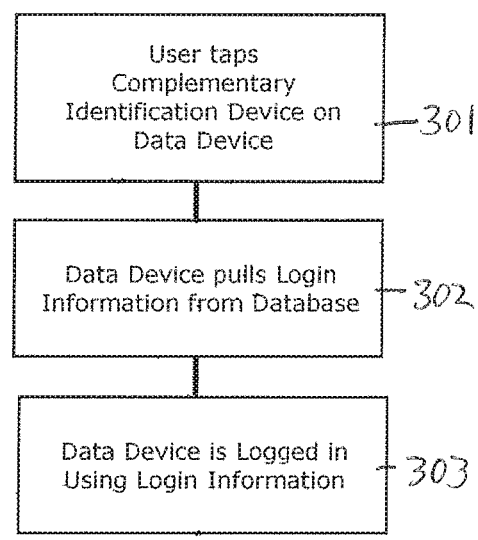
FIG. 3b is an exemplary flowchart illustrating the operation of an automated login initialization system in accordance with the second aspect.

Referring now to FIG. 3B, a flowchart illustrating the exemplary usage of the second aspect of the disclosed embodiment is shown. At block 301, the user may initialize a log-in procedure by first using the complementary identification device 22 to transmit or pass information to the reader 36*a*1 of the data device 36*a*. In one aspect, this may be done by tapping or waving the complementary identification device 22 on or within the vicinity of the reader 36*a*1. This may be achieved, as previously noted, for example, with data stored within RFID tags, NFC chips, Bluetooth modules, RF transmitters or IR transmitters, or optical or printed indicia. The data transmitted or passed to reader 36*a*1 of the data device 36*a* may include, for instance, log-in identification data, or any other suitable data desirable to facilitate a log-in procedure as discussed above. Using the data received from the complementary identification device 22, the data device may access the login database 112 located on the backend 11 via the network 12. This process may be controlled by the login management application 114. For example, the data device 36*a* may download login information associated with the data received from the complementary identification device 22. This may include identification data, personalized settings data, personalized user information or any suitable data specific to a data device desirable to facilitate the log-in procedure. At block 303, the data device 36*a* uses the data received from login database 112 to complete the log-in procedure, thus allowing the user to access the data device 36*a* so that all of the user's personalized settings and data are now accessible on the data device 36*a*1.

Referring now to FIG. 4A, a third aspect of the Quick Launch system is shown. For simplicity and ease of understanding, the remainder of the application will be discussed with respect to data device 46*a*, although what is disclosed is equally applicable to any data device 46*a-n*. Data devices 46*a-n* are substantially similar to data devices 16*a-n* as described above. The third aspect includes a reader device 41 substantially similar to reader device 21 as previously noted with regard to FIG. 2A. The reader device 41 may have a reader 41*b* configured to read data from a complementary identification device 22 substantially as described previously as well as a processor 41*c* substantially corresponding to processor 21*ca* described previously. In one aspect of the disclosed embodiment, the reader 41*b* may be an RFID reader. However, in other aspects of the disclosed embodiment, the data reader 41*b* may also be a Near Field Communication (NFC) data reader, a Bluetooth module, a radio frequency (RF) reader, infrared (IR) receiver, or any suitable reader capable of receiving transmitted data information. In yet alternate aspects of the disclosed embodiment, the reader 41*b* may also be a camera or optical scanner configured to read visual indicia including barcodes, Quick Response (QR) codes, matrix bar codes, Microsoft Tags, or any other suitable visual or printed indicia. In one aspect, the reader device 41 may be any suitable device capable of reading data and may not be dedicated reader specifically for use in login procedures. In yet alternate embodiments, the reader 41 may also be configured to read any other data, including, for instance, magnetic stripes. The reader 41*b* may also be configured to read data from a data device 46*a*. Specifically, the reader 41*b* may read data located on a data device tag 46*a*1 which is coupled or otherwise placed on the data device 46*a*. Such a data device tag 46*a*1 may contain any data which uniquely identifies the data device 46*a*. The reader device 41 may further be configured to access a login database 112 located on backend 11 via the network 12.

Figure 4B:
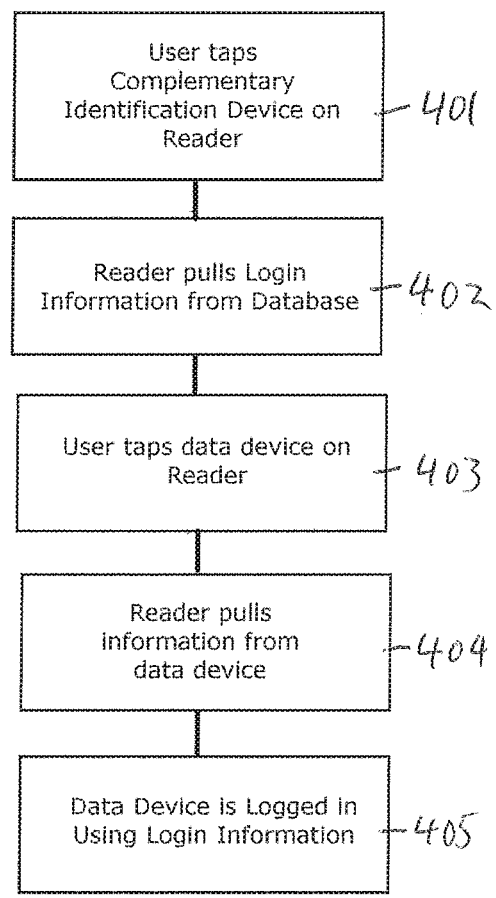
FIG. 4b is an exemplary flowchart illustrating the operation of an automated login initialization system in accordance with the third aspect.

Referring now to FIG. 4B, a flowchart illustrating the exemplary usage of the third aspect of the disclosed embodiment is shown. At block 401, a user may initialize a log-in procedure by first using the complementary identification device 22 to transmit or pass information to the reader device 41 substantially similar to the methods previously described. For example, this may be done by tapping or waving the complementary identification device 22 on or within the vicinity of the reader 41*b*. This may be achieved, as previously noted, for example, with data stored within RFID tags, NFC chips, Bluetooth modules, RF transmitters or IR transmitters, or optical or printed indicia, or any other suitable means. The data transmitted or passed to reader 41*b* of the reader device 41 may include, for instance, log-in identification data, or any other suitable data desirable to facilitate a log-in procedure as discussed above. At block 402, the reader device 41 may access the login database 112 to retrieve credential or identification information related to the information received from the complementary identification device 22. This process may be managed by the login management application 114. For example, the information may include information about personalized user settings, personalized user data or other personalized data desirable to complete a login procedure. In alternate aspects, the login database 112 may also be used to verify login data received from the complementary identification device 22 to facilitate a login. In yet other aspects of the disclosed embodiment, the login database 112 may be accessed for any other suitable data desirable to facilitate a user to log into a data device 46*a*. At block 403, the user may further transmit or pass information from the data device tag 46*a*1 of the data device 46a to the reader 41b. The information transmitted from the data device tag 46a1 may be in a substantially similar data format as transmitted by the complementary identification device 22. For example, the data device tag 46a1 may be, in one aspect of the disclosed embodiment, an RFID tag uniquely identifying the data device tag 46ba. In other aspects, the data device tag 46a1 may include NFC chips, RF modules, Bluetooth modules, visual and printed indicia, or any suitable means of passing information capable of uniquely identifying a data device 46a. At block 404, the reader device 41 may further access the login database 112 to retrieve information related to the data received from the data device tag 46a1. For example, this may be any data suitable to initiate a pairing operation between the user and the data device 46a. At block 405, the login operation is completed by pushing the credential or identification information from the login database 112 to the data device 46a identified by the identification data stored on data device tag 46a1.

Referring now to FIG. 5A, an exemplary schematic diagram of a fourth aspect of the automated login system is shown. A reader device 51 is disclosed substantially similar to reader devices 21 and 41 as previously disclosed. The reader device 51 may also have a reader 51b which is also substantially similar to readers 21b and 41b as previously disclosed. For example, in one aspect of the disclosed embodiment, the reader 51b may be an RFID reader. However, in other aspects of the disclosed embodiment, the data reader 51b may also be a Near Field Communication (NFC) data reader, a Bluetooth module, a radio frequency (RF) reader, infrared (IR) receiver, or any suitable reader capable of receiving transmitted data information. In yet alternate aspects of the disclosed embodiment, the reader 51b may also be a camera or optical scanner configured to read visual indicia including barcodes, Quick Response (QR) codes, matrix bar codes, Microsoft Tags, or any other suitable visual or printed indicia, including, for example, magnetic stripe. In one aspect, the reader device 51 may be any suitable device capable of reading data and may not be dedicated reader specifically for use in login procedures. The reader 51 may be configured to read an identification tag 56a which is connected to, or is part of, data device 56. Data device 56 may be substantially similar to data devices 16, 36a-n and 46a-n as described previously. The identification tag 56a may generally replace the complementary identification device 22, but otherwise contains substantially similar data and using substantially similar transfer technology. In other aspects, the identification tag 56a may also contain identification information of the data device 56 similar to that of data device tag 46a1. The data reader 51 may be configured to access a login database 112 located on backend 11 via the network 12.

Figure 5B:
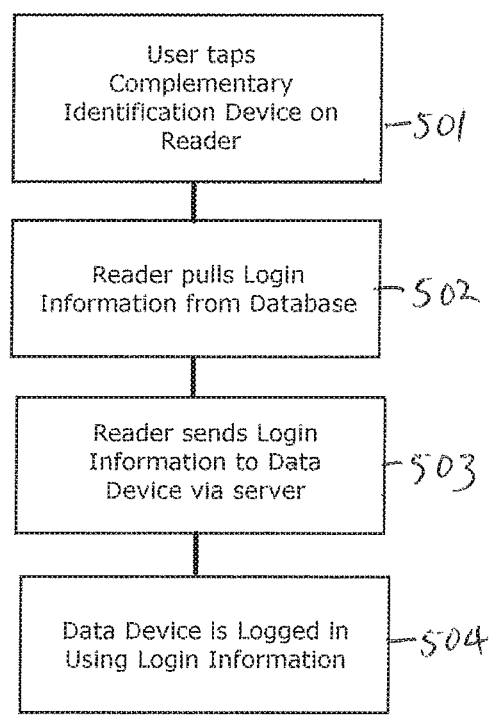
FIG. 5b is an exemplary flowchart illustrating the operation of an automated login initialization system in accordance with the fourth aspect.

Referring now to FIG. 5B, a flowchart illustrating the exemplary usage of the fourth aspect of the disclosed embodiment is shown. At block 501, a user may initialize a log-in procedure by first using the identification tag 56a to transmit or pass information to the reader 51b of the reader device 51 substantially similar to the methods previously described. For example, this may be done by tapping or waving the identification tag 56a on or within the vicinity of the reader 41b. This may be achieved, as previously noted, for example, with data stored within RFID tags, NFC chips, Bluetooth modules, RF transmitters or IR transmitters, or optical or printed indicia. The data transmitted or passed to reader 51b of the reader device 51 may include, for instance, log-in identification data, or any other suitable data desirable to facilitate a log-in procedure as discussed above. The data may further include, for instance, identification information related to the data device 56 associated with the identification tag 56a and the user. At block 502, the reader device 51 may access the login database 112 to retrieve credential or identification information related to the information received from the identification tag 56a. As noted previously, this process may be controlled by the login management application 114. For example, the information may include information about personalized user settings, personalized user data or other personalized data desirable to complete a login procedure. In alternate aspects, the login database 112 may also be used to verify login data received from the complementary identification device 22 to facilitate a login. In yet other aspects of the disclosed embodiment, the login database 112 may be accessed for any other suitable data desirable to facilitate a user to log into a data device 56. At block 503, the reader device 51 facilitates a server push of login data to data device 56 or otherwise logs the user in using the data received from the login database 112 to the data device 56 from the server. In yet alternate embodiments, the reader device 51 may merely unlock certain functionalities within the data device 56 upon login rather than pushing data received from the login database 112 to the data device 56.

It should be understood that the foregoing description is only illustrative of the aspects of the disclosed embodiment and that the aspects of the disclosed embodiment can be used individually or in any suitable combination thereof. Various alternatives and modifications can be devised by those skilled in the art without departing from the aspects of the disclosed embodiment. Accordingly, the aspects of the disclosed embodiment are intended to embrace all such alternatives, modifications and variances.

In a first aspect of the disclosed embodiments, a system for automating a data device login procedure is disclosed. The system having a network, a system backend communicable with the network, comprising a backend processor configured to control a simplified login procedure and a database of login information accessible by the backend processor, where the system backend is shared and is not dedicated to control a login procedure, at least one data reader communicable with the system backend via the network configured to receive a credential data from at least one identification device, where the at least one data reader is configured for effecting access to a different system via the at least one identification device, and at least one fungible portable data device communicable with the backend via the network configured to receive a login information from the system backend for completing a login procedure. The at least one data reader is further configured to initiate the login procedure upon receipt of the credential data from the at least one identification device and further configured to communicate the credential data to the system backend via the network. The system backend is further configured to determine the login information associated with the credential data from the database of login information, the login information associated with the credential data comprising personalization information for the fungible portable data device and the system backend completes the login procedure to at the at least one fungible portable data device via the network.

In accordance with the first aspect of the disclosed embodiment, the system backend is further configured to complete the login procedure for the at least one fungible portable data devices with the login information associated with the credential data concurrent with access to the different system.

In accordance with the first aspect of the disclosed embodiment, the at least one data reader is shared by the system and the different system.

In accordance with a second aspect of the disclosed embodiment, the at least one identification device is a dedicated identification device.

In accordance with the second aspect of the disclosed embodiment, the one of the at least one fungible portable data devices utilizes the login information to personalize at least one function of the at least one fungible portable data device.

In accordance with a third aspect of the disclosed embodiment, the at least one identification device is integral with the at least one fungible portable data devices.

In accordance with the third aspect of the disclosed embodiment, the one of the at least one fungible portable data devices utilizes the login information to personalize at least one function of the at least one fungible portable data device.

In accordance with a fourth aspect of the disclosed embodiment, the at least one data reader is integral with the at least one fungible portable data devices.

In accordance with the fourth aspect of the disclosed embodiment, the one of the at least one fungible portable data devices utilizes the login information to personalize at least one function of the at least one fungible portable data device.

In accordance with a fifth aspect of the disclosed embodiment, the at least one data reader further comprises a locator device configured to detect the at least one fungible portable data devices within the vicinity of the at least one data reader.

In accordance with the fifth aspect of the disclosed embodiment, the system is further configured to complete a login procedure with the at least one fungible portable data devices detected by the locator device.

In accordance with the fifth aspect of the disclosed embodiment, the system is further configured to complete a login procedure with the at least one fungible portable data devices detected by the locator device, wherein the at least one fungible portable data device is activated by a user.

In accordance with the fifth aspect of the disclosed embodiment the one of the at least one fungible portable data devices utilizes the login information to personalize at least one function of the at least one fungible portable data device.

In accordance with the first aspect of the disclosed embodiment, the at least one function is personalized settings associated with a login information.

In accordance with the first aspect of the disclosed embodiment, the at least one function is messages associated with a login information.

In accordance with a sixth aspect of the disclosed embodiment, the at least one data reader is configured to complete the login procedure with the credential data and a phone identification data.

In accordance with the sixth aspect of the disclosed embodiment, the phone identification data is received from the at least one fungible portable data device.

In accordance with the sixth aspect of the disclosed embodiment, the one of the at least one fungible portable data devices utilizes the login information to personalize at least one function of the at least one fungible portable data device.

In accordance with an eighth aspect of the disclosed embodiment, a method for automating a data device login procedure is provided, the method having receiving, via at least one data reader, a credential data from at least one identification device, initiating a login procedure, via the at least one data reader, upon receipt of the credential data from the at least one identification device and further communicating the credential data to the system backend via the network, determining a login information associated with the credential data from a database of login information, and completing the login procedure with at least one fungible data devices via the network utilizing the login information to personalize at least one function of the at least one fungible data device.

In accordance with an ninth aspect of the disclosed embodiment, a non-transitory computer readable medium having computer readable program code embodied therein comprising computer readable code is disclosed. The non-transitory computer readable medium having computer readable program code embodied therein comprising computer readable code that, when executed, performs receiving, via at least one data reader, a credential data from at least one identification device, initiating a login procedure, via the at least one data reader, upon receipt of the credential data from the at least one identification device and further communicating the credential data to the system backend via the network, determining a login information associated with the credential data from a database of login information, and completing the login procedure with at least one fungible portable data device via the network utilizing the login information to personalize at least one function of the at least one fungible portable data device.

It should be understood that the exemplary embodiments disclosed herein can be used individually or in any suitable combination thereof. It should also be understood that the foregoing description is only illustrative of the embodiments. Various alternatives and modifications can be devised by those skilled in the art without departing from the embodiments. Accordingly, the present embodiments are intended to embrace all such alternatives, modifications and variances that fall within the scope of the appended claims.

What is claimed is:

1. A system, comprising:
a memory configured to store computer-executable instructions; and
a processor configured to access the memory and execute the computer-executable instructions to perform operations comprising:
  receiving credential data associated with a user from a data reader, the credential data collected from at least one identification device associated with the user;
  identifying login information associated with the credential data;
  determining a portable data device from among a plurality of portable data devices based at least in part on information from a locator device, the locator device being located adjacent to the data reader, the information indicating a proximity of the determined portable data device with respect to the locator device; and
  initiating a login procedure on the determined portable data device based on the login information, the login procedure logging the user in to the determined portable data device and unlocking a first functionality of the determined portable data device.

2. The system of claim 1, wherein the operations further comprise unlocking a second functionality of the determined portable data device based on the login information.

3. The system of claim 1, wherein identifying the login information associated with the credential data comprises accessing a login database that stores the login information and personalization settings data.

4. The system of claim 3, wherein initiating the login procedure on the determined portable data device is further based on the personalization settings data.

5. The system of claim 1, wherein initiating the login procedure comprises:
   sending the login information to the determined portable data device; and
   enabling the determined portable data device to log in the user without input from the user at the determined portable data device.

6. The system of claim 1, wherein the plurality of portable data devices include fungible portable data devices.

7. The system of claim 1, wherein the locator device is separate from the data reader.

8. A computer-implemented method, comprising:
   receiving credential data associated with a user from a data reader, the credential data collected from at least one identification device associated with the user;
   identifying login information associated with the credential data;
   determining a portable data device from among a plurality of portable data devices based at least in part on information from a locator device, the locator device being located adjacent to the data reader, the information indicating a proximity of the determined portable data device with respect to the locator device; and
   initiating a login procedure on the determined portable data device based on the login information, the login procedure logging the user in to the determined portable data device and unlocking a first functionality of the determined portable data device.

9. The computer-implemented method of claim 8, wherein:
   the method further comprises receiving status data associated with the plurality of portable data devices; and
   determining the portable data device is further based on the status data.

10. The computer-implemented method of claim 8, wherein completion of the login procedure is dependent on removal of the determined portable data device from a docking station.

11. The computer-implemented method of claim 10, further comprising:
   detecting that the determined portable data device has been returned to the docking station; and
   initiating a log out procedure on the determined portable data device based on detecting that the determined portable data device has been returned to the docking station, the log out procedure logging the user out of the determined portable data device.

12. The computer-implemented method of claim 8, further comprising unlocking a second functionality of the determined portable data device based on the login information.

13. The computer-implemented method of claim 8, wherein identifying the login information associated with the credential data comprises accessing a login database that stores the login information and personalization settings data.

14. The computer-implemented method of claim 8, wherein initiating the login procedure comprises:
   sending the login information to the determined portable data device; and
   enabling the determined portable data device to log in the user without input from the user at the determined portable data device.

15. The computer-implemented method of claim 8, wherein the data reader is configured to collect the credential data from the at least one identification device as the at least one identification device is scanned by the data reader.

16. One or more non-transitory computer-readable media comprising computer-executable instructions that, when executed by one or more computer systems, cause the one or computer systems to perform operations comprising:
   receiving credential data associated with a user from a data reader, the credential data collected from at least one identification device associated with the user;
   identifying login information associated with the credential data;
   determining a portable data device from among a plurality of portable data devices based at least in part on information from a locator device, the locator device being located adjacent to the data reader, the information indicating a proximity of the determined portable data device with respect to the locator device; and
   initiating a login procedure on the determined portable data device based on the login information, the login procedure logging the user in to the determined portable data device and unlocking a first functionality of the determined portable data device.

17. The one or more non-transitory computer-readable media of claim 16, wherein the operations further comprise unlocking a second functionality of the determined portable data device based on the login information.

18. The one or more non-transitory computer-readable media of claim 17, wherein the second functionality comprises an application of the determined portable data device.

19. The one or more non-transitory computer-readable media of claim 16, wherein identifying the login information associated with the credential data comprises accessing a login database that stores the login information and personalization settings data.

20. The one or more non-transitory computer-readable media of claim 16, wherein the determined portable data device comprises a non-fungible portable data device.

* * * * *